United States Patent [19]
Stivland et al.

[11] Patent Number: 6,102,890
[45] Date of Patent: Aug. 15, 2000

[54] CATHETER HAVING IMPROVED PROXIMAL SHAFT DESIGN

[75] Inventors: Timothy M. Stivland, Plymouth; Elias A. Khoury, Champlin, both of Minn.

[73] Assignee: SciMed Life Systems, Inc., Maple Grove, Minn.

[21] Appl. No.: 09/178,201

[22] Filed: Oct. 23, 1998

[51] Int. Cl.$^7$ .............................................. A61M 29/00
[52] U.S. Cl. ............................................. 604/96; 604/99
[58] Field of Search ................... 604/96, 282, 95, 604/53; 606/194

[56] References Cited

U.S. PATENT DOCUMENTS

| | | | |
|---|---|---|---|
| 2,687,131 | 8/1954 | Raiche | 123/349 |
| 2,936,760 | 5/1960 | Gants | 123/349 |
| 3,225,762 | 12/1965 | Guttman | 128/214 |
| 3,884,242 | 5/1975 | Bazell et al. | 128/351 |
| 4,044,765 | 8/1977 | Kline | 128/214.4 |

(List continued on next page.)

FOREIGN PATENT DOCUMENTS

| | | |
|---|---|---|
| 0 344 503 A1 | 12/1989 | European Pat. Off. . |
| 0 365 993 A1 | 5/1990 | European Pat. Off. . |
| 0 368 523 A2 | 5/1990 | European Pat. Off. . |
| 0 380 873 B1 | 5/1990 | European Pat. Off. . |
| 0 380 873 A2 | 8/1990 | European Pat. Off. . |
| 0 380 873 A3 | 8/1990 | European Pat. Off. . |
| 1251-914 | 8/1986 | U.S.S.R. . |

OTHER PUBLICATIONS

Paul G. Yock, U.S. Patent Application Serial No. 852,197, Filed Apr. 15, 1986.

"USCI Lo Profile II Balloon Dilatation Catheters," C.R. Card, Inc. 1987.

"Until Someone Does It, No One Thinks It Can Be Done," C.R. Bard, Inc., 1988.

Schneider–Shiley, brochure entitled *Monorail–Bonzel Coronary Dilatation System*, published on date even with or prior to Nov. 23, 1994.

*Monorail–Piccolino*, Flyer, Oct., 1988.

*ACS RX™ Dilatation Catheters*, Flyer, Mar., 1989.

*Balloon Catheters for Percutaneous Insertion Into the Vascular System*, Björn Nordenström, Mar. 2, 1962.

"New Instruments for Catheterization and Angiocardiography," Björn Nordenström, Jul.–Dec. 1965 Issue of *Radiology*.

*Primary Examiner*—Michael Buiz
*Assistant Examiner*—Anthony King
*Attorney, Agent, or Firm*—Crompton, Seager & Tufte, LLC

[57] ABSTRACT

A catheter and subassemblies for catheters having improved proximal regions, and mid-regions including hypotube having distally increasing flexibility. One catheter has a kink resistant proximal shaft not including hypotube and including an outer tube disposed over a braid disposed over an inner tube. One catheter includes a proximal shaft having a 12-inch long strain relief disposed about a tubular region formed of hypotube. Another catheter includes a proximal hypotube shaft having a set curve imparted through bending and annealing, resulting in a catheter hypotube shaft having reduced spring and decreased kink radius. A catheter subassembly includes a hypotube shaft having a helical cut into the hypotube wall to increase flexibility over the length of the cut. One helical cut extends through the hypotube wall and includes a polymeric sleeve thereover to allow the cut hypotube to function as an inflation fluid delivery tube.

19 Claims, 3 Drawing Sheets

U.S. PATENT DOCUMENTS

| | | | |
|---|---|---|---|
| 4,289,128 | 9/1981 | Rüsch | 128/207.15 |
| 4,425,919 | 1/1984 | Alston, Jr. et al. | 128/658 |
| 4,468,224 | 8/1984 | Enzmann et al. | 604/247 |
| 4,597,755 | 7/1986 | Samson et al. | 604/96 |
| 4,662,368 | 5/1987 | Hussein et al. | 128/303.1 |
| 4,705,507 | 11/1987 | Boyles | 604/101 |
| 4,719,924 | 1/1988 | Crittenden et al. | 128/772 |
| 4,748,982 | 6/1988 | Horzewski et al. | 128/344 |
| 4,762,129 | 8/1988 | Bonzel | 128/344 |
| 4,771,777 | 9/1988 | Horzewski et al. | 128/344 |
| 4,798,598 | 1/1989 | Bonello et al. | 604/280 |
| 4,820,349 | 4/1989 | Saab | 128/344 |
| 4,824,435 | 4/1989 | Giesy et al. | 604/49 |
| 4,838,268 | 6/1989 | Keith et al. | 128/344 |
| 4,846,174 | 7/1989 | Willard et al. | 128/344 |
| 4,877,031 | 10/1989 | Conway et al. | 128/344 |
| 4,881,547 | 11/1989 | Danforth | 128/344 |
| 4,896,670 | 1/1990 | Crittenden | 606/194 |
| 4,906,241 | 3/1990 | Noddin et al. | 606/194 |
| 4,917,088 | 4/1990 | Crittenden | 606/194 |
| 4,921,478 | 5/1990 | Solano et al. | 604/53 |
| 4,928,693 | 5/1990 | Goodin et al. | 128/637 |
| 4,940,062 | 7/1990 | Hampton et al. | 128/772 |
| 4,943,278 | 7/1990 | Euteneuer et al. | 604/96 |
| 4,944,745 | 7/1990 | Sogard et al. | 606/194 |
| 4,946,466 | 8/1990 | Pinchuk et al. | 606/194 |
| 4,953,553 | 9/1990 | Tremulis | 128/637 |
| 4,976,690 | 12/1990 | Solar et al. | 604/96 |
| 4,976,720 | 12/1990 | Machold et al. | 606/194 |
| 4,988,356 | 1/1991 | Crittenden et al. | 606/192 |
| 4,994,032 | 2/1991 | Sugiyama et al. | 604/96 |
| 4,998,917 | 3/1991 | Gaiser et al. | 604/96 |
| 4,998,923 | 3/1991 | Samson et al. | 606/194 |
| 5,032,113 | 7/1991 | Burns | 604/96 |
| 5,034,001 | 7/1991 | Garrison et al. | 604/53 |
| 5,035,686 | 7/1991 | Crittenden et al. | 604/96 |
| 5,035,705 | 7/1991 | Burns | 606/194 |
| 5,040,548 | 8/1991 | Yock | 178/848 |
| 5,042,985 | 8/1991 | Elliot et al. | 606/192 |
| 5,047,045 | 9/1991 | Arney et al. | 606/194 |
| 5,050,606 | 9/1991 | Tremulis | 128/637 |
| 5,057,120 | 10/1991 | Farcot | 606/194 |
| 5,061,273 | 10/1991 | Yock | 606/194 |
| 5,102,390 | 4/1992 | Crittenden et al. | 604/96 |
| 5,102,403 | 4/1992 | Alt | 604/280 |
| 5,112,304 | 5/1992 | Barlow et al. | 604/96 |
| 5,156,594 | 10/1992 | Keith | 604/96 |
| 5,169,386 | 12/1992 | Becker et al. | 604/49 |
| 5,176,637 | 1/1993 | Sagae | 604/96 |
| 5,180,367 | 1/1993 | Kontos et al. | 604/101 |
| 5,242,396 | 9/1993 | Evard | 604/96 |
| 5,346,505 | 9/1994 | Leopold | 606/194 |
| 5,395,332 | 3/1995 | Ressemann et al. | 604/96 |
| 5,425,711 | 6/1995 | Ressemann et al. | 604/96 |
| 5,449,343 | 9/1995 | Samson et al. | 604/96 |
| 5,520,645 | 5/1996 | Imran et al. | 604/95 |
| 5,599,326 | 2/1997 | Carter | 604/282 |
| 5,643,209 | 7/1997 | Fugoso et al. | 604/96 |
| 5,695,468 | 12/1997 | Lafontaine et al. | 604/99 |
| 5,702,439 | 12/1997 | Keith et al. | 604/96 |
| 5,715,825 | 2/1998 | Crowley | 600/467 |
| 5,725,513 | 3/1998 | Ju et al. | 604/280 |
| 5,728,067 | 3/1998 | Enger | 604/102 |
| 5,785,685 | 7/1998 | Kugler et al. | 604/96 |
| 5,795,341 | 8/1998 | Samson | 604/264 |
| 5,908,405 | 6/1999 | Imran et al. | 604/53 |
| 5,911,715 | 6/1999 | Berg et al. | 604/525 |
| 5,951,539 | 9/1999 | Nita et al. | 604/526 |

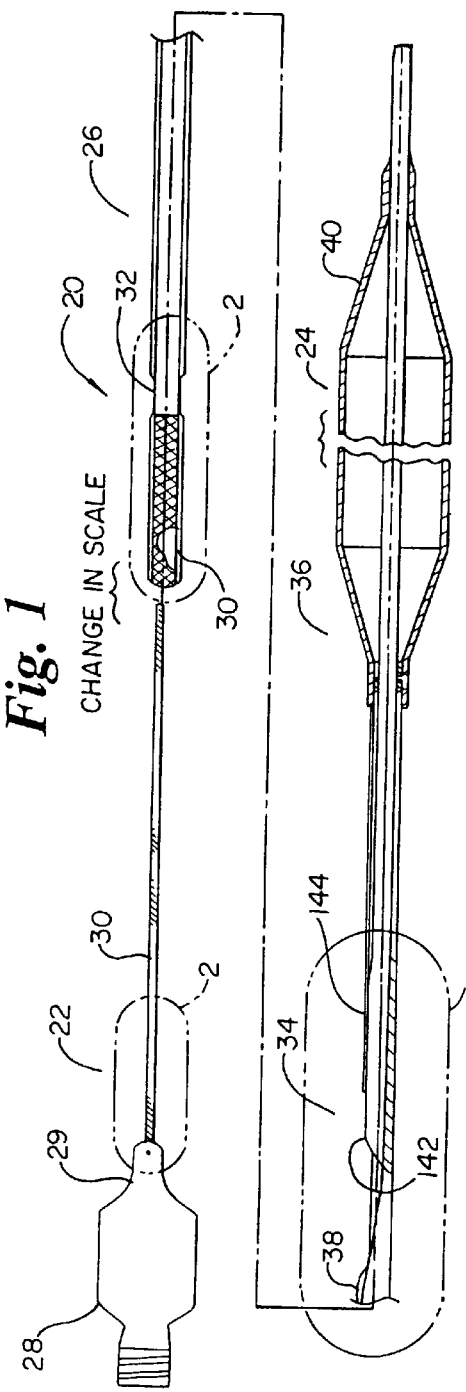
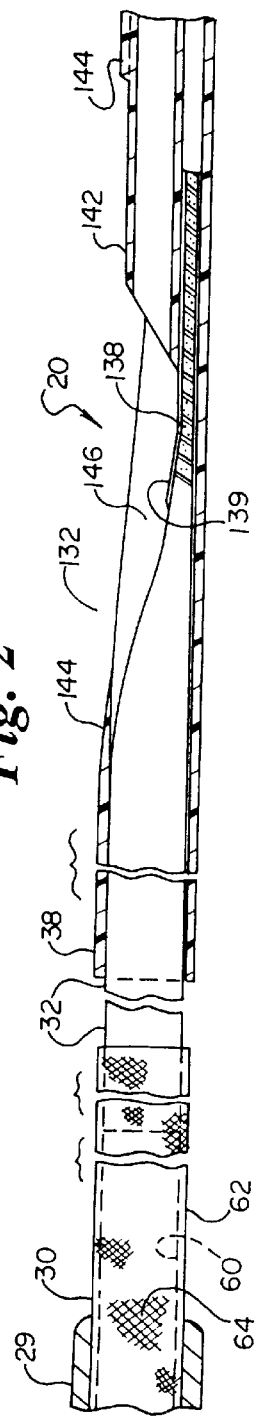
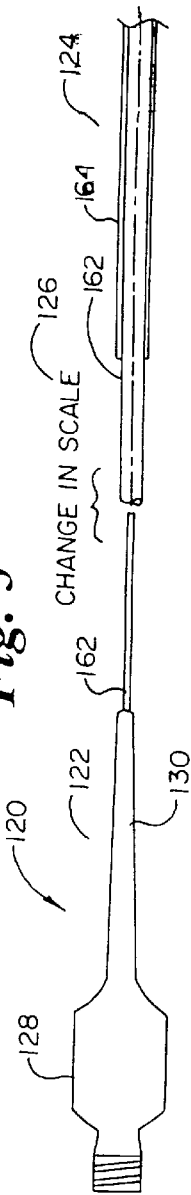
Fig. 1
Fig. 2
Fig. 3

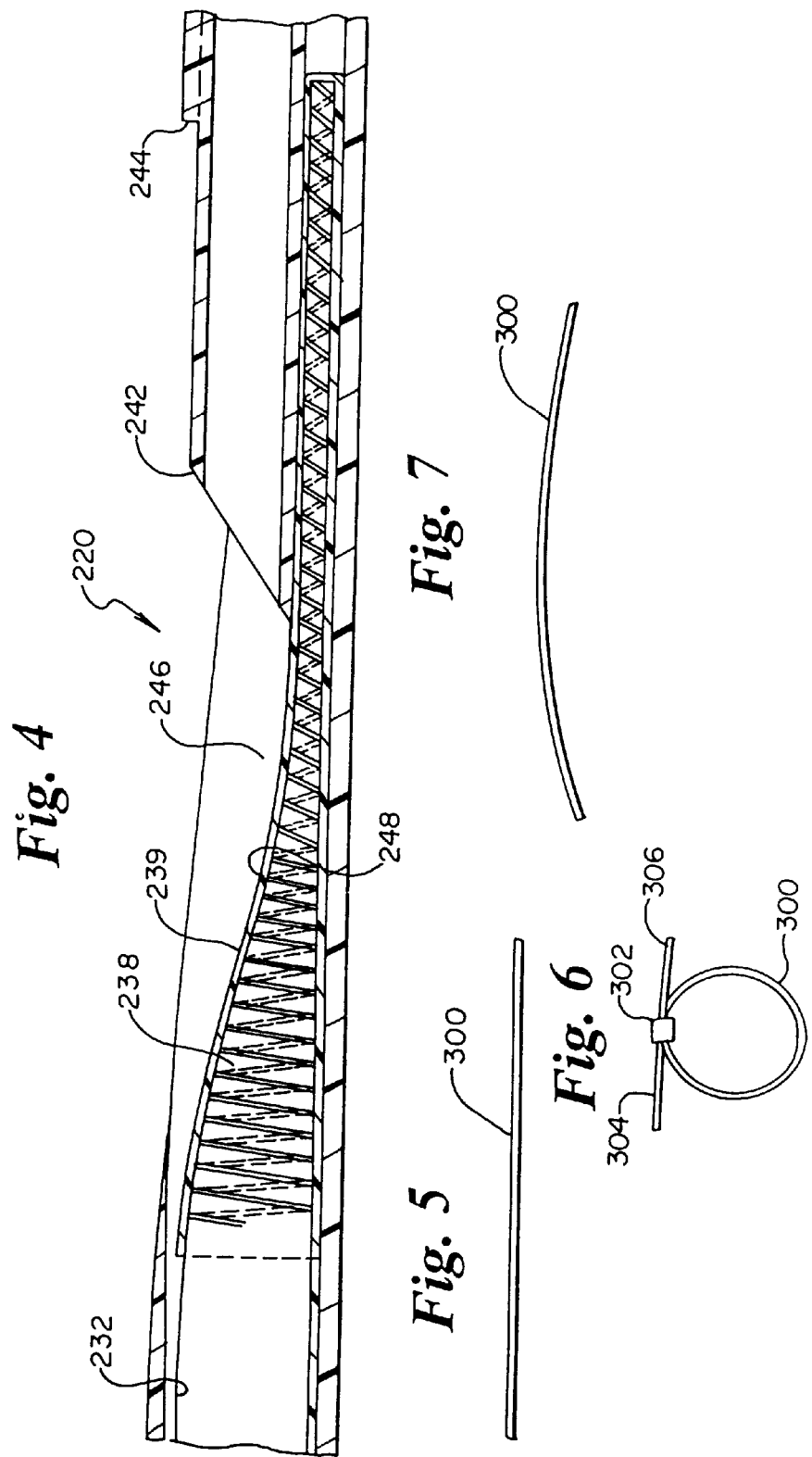

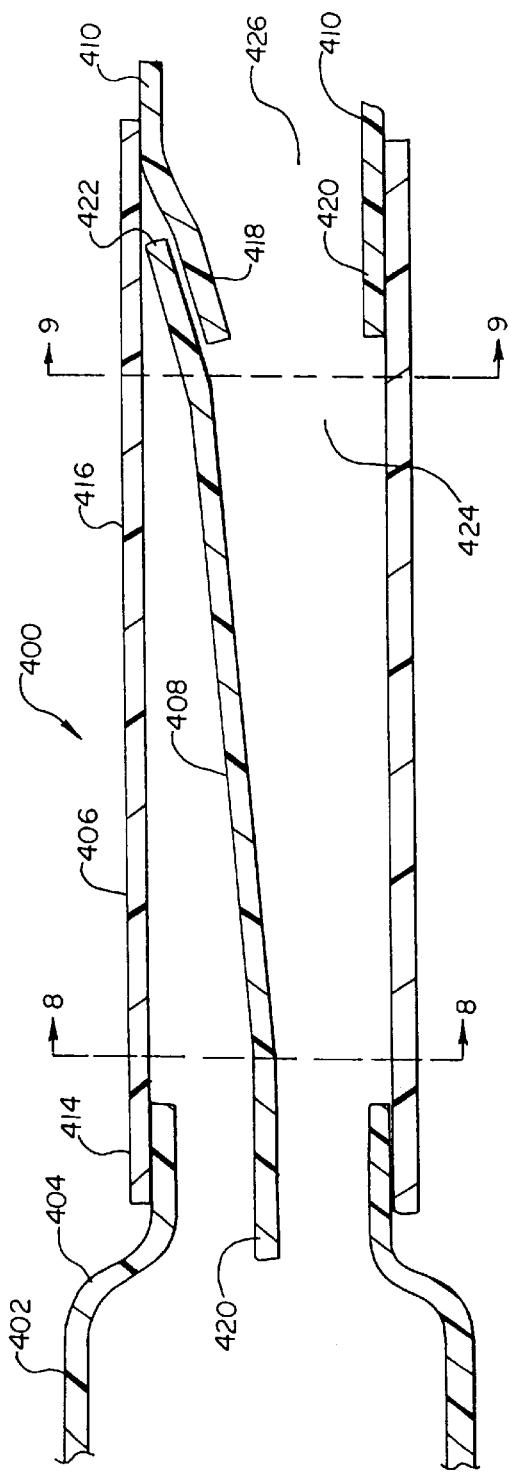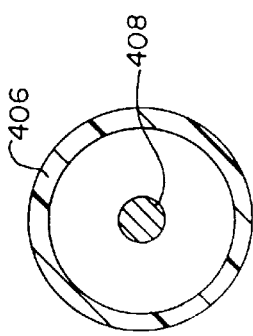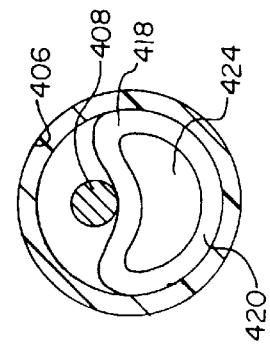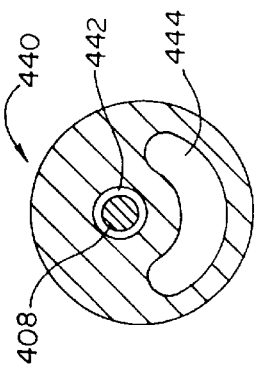

CATHETER HAVING IMPROVED PROXIMAL SHAFT DESIGN

FIELD OF THE INVENTION

The present invention relates generally to medical devices. More specifically, the present invention relates to catheters having improved proximal shaft designs. In particular, the invention includes kink-resistant proximal shafts, proximal shafts having less spring, and shafts having distally increasing flexibility.

BACKGROUND OF THE INVENTION

Angioplasty procedures have gained wide acceptance in recent years as efficient and effective methods for treating types of vascular disease. In particular, angioplasty is widely used for opening stenoses in the coronary arteries and is used for treating stenoses in other vascular regions.

One widely used form of angioplasty makes use of a dilatation catheter which has a inflatable balloon at the distal end and a guide wire lumen within at least a portion of the catheter shaft. Typically, a guide wire is inserted through the vascular system to a position near the stenoses, leaving a proximal portion of the guide wire extending from the patient. The proximal guide wire portion is threaded through the dilatation catheter guide wire lumen and the dilatation catheter advanced through the vascular system over the guide wire to the position near the stenoses. The treating physician manipulates the dilatation catheter until the balloon is positioned across the stenoses. The balloon is then inflated by supplying fluid under pressure through an inflation lumen in the catheter to the balloon. The inflation of the balloon widens the lumen through the stenosed area by pressing the inflating balloon wall against the lesion inside wall.

Current angioplasty catheters often have a short strain relief surrounding a hypotube segment that forms the proximal shaft of the catheter. Hypotube, or thin-walled hypodermic tubing, has many desirable characteristics, but can kink if bent too sharply. Strain reliefs are commonly formed of a polymeric material extending distally from a manifold affixed to the proximal end of a catheter shaft. The current designs can inhibit kinking where the hypotube exits the manifold within the strain relief. Existing strain reliefs commonly have a length of about 1 to 2 inches. Some catheters are returned by users, having kinked proximal shaft regions in spite of the existing strain reliefs. Applicants believe catheter proximal shaft designs could be improved to further reduce kinking.

Catheters have flexibility requirements that vary with the location along the catheter length. Less flexibility may be required in the catheter proximal portion, where the catheter may lie within a large inside diameter, straight vessel portion. Greater flexibility is often a design goal in the catheter distal portion, where traversing small inside diameter, tortuous vessels may be required. In the catheter mid-region, a gradually, distally increasing flexibility is desirable rather than an abrupt change from low to high flexibility. What would be desirable is a catheter including a mid-region having a distally increasing flexibility while retaining the advantages of hypotube.

Present catheters having hypotube proximal shafts have the advantages of hypotube and one disadvantage of hypotube, that of sometimes excessive springiness. In use, current catheters can exhibit a large amount of spring or whipping about of the unconstrained portion. This can make handling the catheter somewhat difficult in the operating room. What would be desirable is a catheter having the advantages of a proximal hypotube portion but without the spring of current hypotube shafts.

SUMMARY OF THE INVENTION

The present invention includes catheters and subassemblies for catheters having improved proximal regions, and mid-regions including hypotube having distally increasing flexibility. One catheter has a kink-resistant proximal shaft including an outer tube disposed over a braid disposed over an inner tube, while not including hypotube in the proximal shaft. One catheter includes a kink-resistant proximal shaft having a 12-inch long strain relief disposed about a hypotube tubular region. Another catheter includes a proximal hypotube shaft having a set curve imparted through bending and annealing, resulting in a catheter hypotube shaft having reduced spring and decreased kink radius. One catheter subassembly includes a hypotube shaft having a cut in the hypotube wall to increase flexibility over the length of the shaft.

Some catheters, according to the present invention, have a braided polymeric proximal shaft in place of a hypotube proximal shaft and provide improved resistance to kinks, which can occur more often than desired in the proximal most 12 inches of catheter. One catheter has a polyethylene inner tube, a stainless steel wire braid over the inner tube, and a polyether block amide (PEBA) tube disposed over the braid. Some catheters, according to the present invention, include a proximal hypotube shaft having a long strain relief disposed over the hypotube to improve the kink resistance. One catheter has a strain relief about 12 inches long disposed over the proximal hypotube portion.

An improved catheter subassembly is provided by the present invention by setting a curve into hypotube for use in a catheter. One method includes wrapping a hypotube into a substantially circular shape, constraining the hypotube into that shape, annealing the hypotube, and releasing the hypotube. The resulting hypotube can have a slight curve imparted to the hypotube. The slight curve improves kink resistance and reduces the spring of the hypotube, while retaining the pushability.

A method for imparting increasing flexibility to a hypotube shaft is provided by the present invention. A hypotube region can have a spiral or helical cut made into the hypotube wall. In one method, the spiral cut extends through the wall. The flexibility of the hypotube can increase with increasing length over the spiral cut. One catheter including the spiral cut hypotube includes a polymeric sleeve disposed over the spiral cut so as to contain fluid within the lumen of the hypotube. One helical cut has decreasing inter-strand distance over the length of the cut, increasing flexibility over the length of the cut.

BRIEF DESCRIPTION OF THE DRAWINGS

FIG. 1 is a longitudinal, cross-sectional view of a catheter including a braided proximal section followed distally by an intermediate hypotube section;

FIG. 2 is an expanded, fragmentary, longitudinal, cross-sectional view of distal selected catheter regions of FIG. 1, illustrating a braided hypotube shaft and a hypotube shaft having a distal spiral cut region;

FIG. 3 is a longitudinal, cross-sectional view of a catheter including a proximal hypotube region having a long strain relief;

FIG. 4 is a fragmentary, longitudinal, cross-sectional view of a distal catheter region including a hypotube shaft having a long distal spiral cut region;

FIG. 5 is a highly diagrammatic view of an unconstrained hypotube section prior to annealing;

FIG. 6 is a highly diagrammatic view of the hypotube section of FIG. 5 constrained in a curve during annealing;

FIG. 7 is a highly diagrammatic view of the hypotube section of FIG. 6 unconstrained after annealing;

FIG. 8 is a fragmentary, longitudinal cross-sectional view of a proximal catheter shaft having a core wire within;

FIG. 9 is a transverse, cross-sectional view take through 8—8 in FIG. 7;

FIG. 10 is a transverse, cross-sectional view taken through 9—9 in FIG. 7; and

FIG. 11 is a transverse, cross-sectional view of a duel lumen extrusion embodiment of a proximal tube.

DETAILED DESCRIPTION OF THE PREFERRED EMBODIMENTS

FIG. 1 illustrates an angioplasty catheter 20 having a proximal region 22, a distal region 24, and a mid-region 26 disposed between the proximal and distal regions. Distal region 24 includes a proximal portion 34 and a distal portion 36. Catheter 20 includes a manifold 28 coupled to a strain relief 29 coupled in turn to a proximal braided shaft 30, which is coupled to a mid-region hypotube shaft 32. Mid-region hypotube shaft 32 is distally coupled to a distal shaft proximal portion 38, which extends distally to a balloon 40. Distal shaft proximal portion 38 includes an outer tube 144 and an inner tube 142. Proximal braided shaft 30 is preferably about twelve (12) inches length, while mid-region hypotube shaft 32 has a preferred length of about thirty-two (32) inches.

Proximal braided shaft 30 preferably includes a polymeric inner tube having a braid thereover and an outer tube formed over the braid. Preferred materials for the inner tube include polyethylene, nylon, PEEK, polyimide, and polytetrafluoroethylene (PTFE) and a preferred braid material is stainless steel wire. One inner tube embodiment is formed of CHRISTAMID™. Preferred outer tube material includes a polyether block amide (PEBA) such as PEBAX™ and a polyamide such as VESTAMID™. Proximal braided shaft 30 can be formed by extruding a polyethylene inner tube and winding stainless steel wire over the recently extruded tube. In a preferred method, wire is braided over the inner tube. In another method, wire is helically wound over the inner tube in one or more passes over the inner tube. The braided tube can then have a PEBA layer extruded over the length of the tube. In one catheter made according to the present invention, the outer tube material is extruded over the braid and allowed to bond through the braid to the inner tube. In one embodiment, a tie-layer material such as PLEXAR™ is applied to the braid material and the outer material is allowed to bond with the tie-layer material, which in turn is allowed to bond with the inner tube material through the braid.

In the embodiment of FIG. 1, the braided proximal braided shaft has replaced the proximal hypotube shaft commonly used in many angioplasty catheters. The proximal braided shaft is believed to greatly reduce the possibility of kinking in the proximal shaft region. In the embodiment illustrated, the use of hypotube is restricted to catheter mid-region 26, where sharp bending is believed to be less of a problem. Hypotube, as the term is used herein, refers generally to a metallic tube having a lumen therethrough. Hypotube is preferably a thin-walled, stainless steel tubing such as used for hypodermic injections.

Referring now to FIG. 2, catheter 20 is illustrated in more detail. Proximal braided shaft 30 is illustrated, including a proximal inner tube 60, a proximal outer tube 60, and an intermediate braid layer 64. Proximal braided shaft 30 extends distally over the proximal end of mid-region hypotube shaft 32, coupling the braided shaft to the hypotube. Mid-region hypotube 32 extends distally within outer tube 144, and continues through a necked or skived portion 146 into a spiral cut region 138. Spiral cut region 138 illustrates another aspect of the present invention. In hypotube mid-region 132, in many embodiments, flexibility remains constant over the length of the hypotube proximal of necked portion 146. In some embodiments, as illustrated in FIG. 2, the hypotube is crimped or buckled to allow insertion of inner guide wire tube 142. Inner guide wire tube 142 is illustrated inserted within outer tube 144. With increasing distal location, increasing distal flexibility is desirable. This increasing flexibility is provided by spiral cut region 138. Spiral cut region 138 is preferably disposed within a polymeric sheath 139.

In one embodiment, spiral cut region 138 includes a single spiral cut entirely through the hypotube wall over the length of the spiral cut region. The spiral cut region can provide increased flexibility relative to the more proximal hypotube region not having the spiral cuts. In one embodiment, the spiral cuts may be viewed as a helix cut through the hypotube wall and having an inter-strand distance between cuts along the length of spiral cut region 138. In one embodiment, the inter-strand distance is substantially constant over the length of the spiral. In this embodiment, applicants believe the spiral cuts have a cumulative effect acting to increase the flexibility of the tube with increasing distal distance. In another embodiment, the inter-strand distance decreases with increasing distal location. In this embodiment, applicants believe the flexibility per unit length increases, and can approach that of a spring, given sufficiently small inter-strand distance. In yet another embodiment, the cuts into the tube wall have increasing depth with increasing distal location. In this embodiment, the proximal portion of the spiral has a cut extending only partially through the tube wall, extending further in the mid-region, and extending entirely through the tube wall in the distal region. Applicants believe this embodiment provides distally increasing flexibility per unit length over the length of the spiral.

Both hypotube mid-region 132 and spiral cut region 138 function as fluid delivery lumens in many embodiments of the invention. In angioplasty catheters, hypotube can contain and deliver balloon inflation fluid. In dye delivery catheters, the hypotube can serve to deliver dye. As the spiral cuts extend through the tube walls in many embodiments, polymeric sleeve 139 can be used to contain fluid that would otherwise escape through the spiral cuts in the tube wall.

Referring now to FIG. 3, a catheter 120 is illustrated, having a proximal region 122, a distal region 124, and a mid-region 126 disposed between the proximal and distal regions. Catheter 120 includes a manifold 128 coupled to a long, proximal strain relief 130. In a preferred embodiment, proximal strain relief 130 is at least six (6) inches long. In a one embodiment, proximal strain relief 130 is about twelve (12) inches long. Strain relief 130 is preferably formed of a polymeric material formed over stainless steel hypotube. Hypotube, as the term is used herein, refers generally to a metallic tube having a lumen therethrough. Preferred polymeric materials include FEP, PTFE, nylon, and PEEK. A preferred strain relief includes a series of ribs and voids well known to those in the art. Strain relief 130, by providing an unusually long strain relief, can provide increased resistance to kinking, especially kinking which might otherwise occur several inches distal of manifold 128.Extending distally from strain relief 130 is hypotube mid-region 162. Hypotube 162 can extend distally into a distal outer tube 164, which can be an outer tube as described with respect to FIGS. 1 and 2.

Referring now to FIG. 4, another catheter 220 is illustrated having a hypotube mid-region 232 extending distally into a spiral cut region 238 disposed within a polymeric sleeve 239. Catheter 220 includes a necked or skived portion 246 and an inner tube 242 extending within an outer tube 244, with inner tube 242 functioning as a guide wire tube and outer tube 244 functioning as part of the catheter distal shaft. Spiral cut region 138 includes a crimped portion 248 within which the hypotube is crimped to make room for entry of inner tube 242 into outer tube 244. In catheter 220, the hypotube is cut both proximal of and distal of necked portion 246. In this embodiment, polymeric sleeve 239 extends both proximal of and distal of necked portion 246. Catheter 220 illustrates an embodiment having a longer spiral cut region than catheter 20 illustrated in FIGS. 1 and 2.

In a preferred embodiment, spiral cut region 138 is formed by cutting into a hypotube section, leaving a proximal portion uncut. In another embodiment, the spiral cut hypotube is provided separately and affixed or welded to the uncut region. While preferred embodiments have spiral cuts, other embodiments have a plurality of distinct cuts over the tube length. The longer spiral cut region provided can provide a longer region of increasing flexibility. In one embodiment, the spiral cut region extends from the middle of mid-region 232 and extends distally therefrom. In another embodiment, the spiral cut region extends over substantially the entire mid-region, starting proximate of the proximal shaft.

Referring now to FIG. 5, a method for decreasing the spring or springiness of catheter hypotube shaft is illustrated. FIG. 5 illustrates a hypotube section 300 in an unconstrained state, having a substantially linear shape. FIG. 6 illustrates hypotube section 300 bent or curved into a constrained state. Lengths of hypotube 304 and 306 are left unconstrained in the method illustrated. In one method, hypotube section 300 is curved into a substantially circular shape and constrained with a clasp 302 as illustrated in FIG. 6. In another method, the hypotube is bent around a mandrel to constrain the hypotube to a desired shape. In one method, hypotube section 300 is annealed while constrained to set a curve in the hypotube. In another method, hypotube section 300 has a curve set by stress relief without necessarily annealing the hypotube. FIG. 7 illustrates hypotube section 300 after the curve has been set.

In one method, the hypotube has a radius of curvature of between one (1) foot and five (5) feet. In a preferred method, the hypotube has a radius of curvature of between one and one-half (1.5) feet and two and one-half (2.5) feet. The hypotube section having the curve set has a reduced springiness and a decreased kink radius. The stiffness can remain substantially the same as the hypotube prior to setting the curve. Applicants believe the pushability of the hypotube having the curve set should remain essentially the same as the untreated hypotube. In a preferred embodiment, proximal and distal lengths of hypotube are left outside of the portion treated to set a curve, as illustrated by lengths 304 and 306 in FIG. 6. Applicants believe optimal results are obtained by allowing a proximal and distal portion of the hypotube to remain straight, not having the set curve imparted to the remainder of the hypotube.

Referring now to FIG. 8, another embodiment of proximal catheter shaft 400 is illustrated. Shaft 400 includes a manifold 402 bonded on a proximal tube or sheath 406 which is coupled to a mid-region tube 410. Proximal tube 406 includes a proximal region 414 and a distal region 416, with proximal region 414 bonded to a manifold distal portion 404, and distal region 416 nested over mid-region tube 410. A core wire or stiffening member 408 is disposed within proximal tube 406. A mid-region tube 410 is illustrated as crimped and nested within proximal tube distal region 416. Mid-region tube 410 can have a proximal portion which is in direct contact with proximal tube 416, as indicated at 420. Mid-region tube 410 can have a proximal portion which is disposed against core wire 408, as indicated at 418.

Core wire 408 includes a proximal end 420 and a distal end 422. Core wire proximal end 420 preferably extends within manifold 402. In one embodiment, core wire 408 is bonded within and to manifold 402. In another embodiment, core wire 408 is not bonded within the manifold. Core wire distal end 422 can be secured between the proximal end of mid-region tube 410 and proximal tube or sheath 406. Proximal tube 406 preferably includes an un-occluded area 424, which can serve as a fluid delivery lumen, for example, as an inflation fluid lumen. Mid-region tube 410 preferably includes an un-occluded area 426, which can be a continuation of area 424, and can also serve as fluid delivery lumen. Core wire 408 is, in one embodiment, not bonded in the mid-region of proximal tube 406, but rather is allowed to float. Preferred materials for forming core wire 408 include stainless steel and Nitinol. Proximal tube 406 includes PEEK in one embodiment. In one embodiment, tube 406 includes an inner layer having a braid about the inner layer and an outer layer about the braid. Mid-region tube 410 is preferably formed of hypotube.

Referring now to FIG. 9, a proximal cross-section of proximal shaft 400 is illustrated. Core wire 408 can be substantially centrally disposed within tube 406 as illustrated. FIG. 10 illustrates a distal cross-section of proximal shaft 400. Core wire 408 is disposed off-center as illustrated, leaving open area 424, which can serve as an inflation lumen. Core wire 408 can be secured off-center by the crimping between mid-region tube 410 and proximal tube 406 as illustrated in FIG. 7. In one embodiment, core wire 408 is bonded within the crimped region illustrated in FIG. 10. In another embodiment, core wire 408 is not bonded in this crimped region.

FIG. 11 illustrates an alternative embodiment for the construction of a catheter proximal shaft such as shaft 400. This embodiment includes a duel lumen extrusion 440. Extrusion 440 can be formed into a tube and has a first lumen 442 and a second lumen 444. First lumen 442 can contain core wire 408 and second lumen 444 can serve as a fluid delivery lumen.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A catheter having a proximal end, a proximal region, a distal region, a distal end, and a mid-region disposed between the proximal and distal regions comprising:

a proximal tubular hypotube shaft having a lumen therethrough;

a manifold disposed near said hypotube shaft proximal end; and a strain-relief extending distally from said manifold, said strain relief having a length of at least about six (6) inches.

2. A catheter as recited in claim 1, wherein said strain relief is disposed about said hypotube proximal portion.

3. A catheter as recited in claim 2, wherein said strain relief includes a polymeric material.

4. A catheter having a proximal end, a proximal region, a distal region, a distal end, and a mid-region disposed between the proximal and distal regions comprising:

a proximal tubular shaft having a distal end and a lumen therethrough;

a mid-region tubular shaft having a lumen therethrough and a proximal end coupled to said proximal tubular shaft distal end; and a distal tubular shaft having a proximal end coupled to said mid-region shaft distal end, wherein said proximal shaft includes a polymeric tube having a braid thereover.

5. A catheter as recited in claim 4, wherein said proximal shaft does not include a hypotube within for at least about the proximal most 12 inches.

6. A catheter as recited in claim 5, wherein said proximal shaft includes an inner polymeric tube, a braid disposed over said inner polymeric tube outside of said proximal shaft distal coupling.

7. A catheter as recited in claim 6, wherein said inner tube includes polymeric material selected from the group consisting of polyethylene, nylon, PEEK, and polyimide, said braid includes metallic wire, and said outer tube includes PEBA.

8. A catheter as recited in claim 5, wherein said mid-region includes hypotube and said proximal shaft does not include hypotube proximal of said mid-region tubular shaft proximal end.

9. A catheter comprising:

a hypotube tubular shaft having a wall, a proximal end and a lumen therethrough; and a proximal shaft having a wall, a lumen therethrough, and a distal end coupled to said hypotube tubular shaft proximal end, wherein said hypotube shaft has at least one spiral cut into said hypotube tubular shaft wall proximate the distal end of the proximal shaft.

10. A catheter as recited in claim 9, wherein said spiral cut extends through said tubular shaft wall and further comprising a polymeric sleeve disposed over said spiral cut.

11. A catheter as recited in claim 10, wherein said at least one spiral cut has a length and inter-strand distances and said inter-strand distances decrease distally over said at least one spiral cut length.

12. A catheter as recited in claim 10, wherein said at least one spiral cut has a length and inter-strand distances and said inter-strand distances are substantially constant over said at least one spiral cut length.

13. A catheter as recited in claim 9, wherein said hypotube shaft includes a distal region and at least one spiral cut into said wall in said distal region.

14. A catheter subassembly as recited in claim 9, wherein the region of the proximal hypotube having the spiral cut is formed separately of, and then bonded to the remainder of the proximal hypotube.

15. A catheter as recited in claim 9, wherein said proximal shaft does not include hypotube.

16. A catheter subassembly having a length including a tubular hypotube region having a tubular wall and at least one cut extending over said length and into said wall.

17. A catheter subassembly as recited in claim 16, wherein said cut includes a helical cut into said wall.

18. A catheter subassembly as recited in claim 17, wherein said cut extends through said tube wall and said subassembly includes a polymeric sleeve disposed over said length.

19. A catheter subassembly as recited in claim 18, wherein said helical cut is formed of at least one helical strand, and said helical strand has inter-strand spacing, and said inter-stand spacing decreases distally over said helical cut, such that said flexibility increases distally over said helical cut.

* * * * *